(12) United States Patent
Gill

(10) Patent No.: US 7,984,929 B2
(45) Date of Patent: Jul. 26, 2011

(54) FLUID CONNECTOR FOR FLUID DELIVERY APPARATUS

(75) Inventor: Steven Streatfield Gill, Bristol (GB)

(73) Assignees: Renishaw PLC, Wotton-Under-Edge (GB); Renishaw (Ireland) Limited, Swords (IE)

( * ) Notice: Subject to any disclaimer, the term of this patent is extended or adjusted under 35 U.S.C. 154(b) by 247 days.

(21) Appl. No.: 12/224,653

(22) PCT Filed: Mar. 12, 2007

(86) PCT No.: PCT/GB2007/000862
§ 371 (c)(1),
(2), (4) Date: Sep. 3, 2008

(87) PCT Pub. No.: WO2007/104961
PCT Pub. Date: Sep. 20, 2007

(65) Prior Publication Data
US 2009/0224529 A1    Sep. 10, 2009

(30) Foreign Application Priority Data
Mar. 13, 2006 (GB) .................................. 0604952.2

(51) Int. Cl.
*A61M 39/00* (2006.01)
(52) U.S. Cl. ............ 285/124.3; 285/124.4; 285/354; 604/905; 604/173
(58) Field of Classification Search ............ 285/305, 285/354, 124.1, 124.2, 124.3, 124.4; 604/905, 604/173, 256
See application file for complete search history.

(56) References Cited

U.S. PATENT DOCUMENTS

| | | | | | |
|---|---|---|---|---|---|
| 3,767,234 | A | * | 10/1973 | Weirich et al. | 285/305 |
| 3,768,844 | A | * | 10/1973 | Goward et al. | 285/305 |
| 3,889,986 | A | * | 6/1975 | Cheshir et al. | 285/124.4 |
| 4,247,135 | A | * | 1/1981 | Weirich et al. | 285/124.4 |
| 4,302,034 | A | * | 11/1981 | Weirich et al. | 285/388 |
| 4,319,772 | A | * | 3/1982 | Weirich et al. | 285/124.5 |
| 4,367,740 | A |   | 1/1983 | Evanoski, III | |

(Continued)

FOREIGN PATENT DOCUMENTS

DE    36 29 858 A1    4/1987
(Continued)

OTHER PUBLICATIONS

U.S. Appl. No. 12/224,655, filed Sep. 3, 2008 in the name of Steven Streatfield Gill.

*Primary Examiner* — David E Bochna
(74) *Attorney, Agent, or Firm* — Oliff & Berridge, PLC

(57) ABSTRACT

A connector is described that comprises a male connector portion that is releasably connectable to a complimentary female connector portion. The male fluid connector portion comprises a plurality of hollow needles that are each in fluid communication with a lumen of the associated tubing. The female connector portion comprises plurality of chambers or apertures that comprise a septum seal through which a hollow needle can be passed. Tubing having a plurality of lumens is coupled to the female connector portion and each lumen is in fluid communication with one of said chambers. The male and/or female connector portions also include an alignment guide that allows the hollow needles of the male part to be uniquely aligned with the corresponding septum seals of the female part. The use of the connector for medical purposes is described.

31 Claims, 6 Drawing Sheets

U.S. PATENT DOCUMENTS

| | | | |
|---|---|---|---|
| 4,367,888 A * | 1/1983 | Leverberg et al. | 285/124.1 |
| 4,382,619 A * | 5/1983 | Grisebach | 285/124.4 |
| 4,534,584 A * | 8/1985 | Weirich et al. | 285/305 |
| 4,581,012 A * | 4/1986 | Brown et al. | 604/175 |
| 4,630,847 A * | 12/1986 | Blenkush | 285/331 |
| 4,673,394 A * | 6/1987 | Fenton et al. | 604/905 |
| 4,695,273 A * | 9/1987 | Brown | 604/173 |
| 4,701,159 A * | 10/1987 | Brown et al. | 604/256 |
| 4,732,139 A | 3/1988 | Kawashima et al. | |
| 4,950,255 A | 8/1990 | Brown et al. | |
| 5,056,829 A * | 10/1991 | Kramer | 285/124.1 |
| 5,197,895 A * | 3/1993 | Stupecky | 285/322 |
| 5,199,947 A * | 4/1993 | Lopez et al. | 604/905 |
| 5,364,377 A | 11/1994 | O'Neil | |
| 5,405,269 A * | 4/1995 | Stupecky | 439/191 |
| 5,478,119 A | 12/1995 | Dye | |
| 5,492,147 A * | 2/1996 | Challender et al. | 604/905 |
| 6,096,011 A * | 8/2000 | Trombley et al. | 604/256 |
| 7,316,424 B2 * | 1/2008 | Kardeis et al. | 285/316 |
| 7,347,853 B2 * | 3/2008 | DiFiore et al. | 604/256 |
| 7,766,394 B2 * | 8/2010 | Sage et al. | 604/905 |
| 2003/0216714 A1 | 11/2003 | Gill | |
| 2009/0030373 A1 * | 1/2009 | Gill | 604/174 |
| 2010/0022967 A1 * | 1/2010 | Mendels | 604/246 |

FOREIGN PATENT DOCUMENTS

| | | |
|---|---|---|
| EP | 0 340 427 A2 | 11/1989 |
| WO | WO 91/10861 A1 | 7/1991 |
| WO | WO 03/077758 A1 | 9/2003 |
| WO | WO 2007/104953 | 9/2007 |

* cited by examiner

| Condition | Type of Agent | Examples | Number of Catheters | Infusion Rate (µl/min) | Required Volume | Pulsed Delivery | Duration of Treatment |
|---|---|---|---|---|---|---|---|
| Parkinson Disease | Growth Factors | GDNF | 2 | 0.5-5 | Striatum | Y | Long-term |
| | Viral Vectors | GDNF Gene | 2 | 0.5-5 | Striatum | N | Short-term |
| | Liposomes | GDNF Gene | 2 | 0.5-5 | Striatum | N | Short-term |
| | Antisense Oligonucleotides | Anti-Parkin Gene | 2 | 0.5-5 | Striatum | N | Long-term |
| | RNA Interference | Anti-Parkin Gene | 2 | 0.5-5 | Striatum | Y | Long-term |
| Alzheimers Disease | Growth Factors | NGF | 4-7 | 5-10 | Nucleus Basalis | Y | Long-term |
| | Viral Vectors | NGF Gene | 4-7 | 5-10 | Nucleus Basalis | N | Short-term |
| | Liposomes | NGF Gene | 4-7 | 5-10 | Nucleus Basalis | N | Short-term |
| Huntingtons Disease | Growth Factors | CNTF | 4-7 | 5-10 | Cerebral Hemispheres | Y | Long-term |
| | Viral Vectors | CNTF Gene | 4-7 | 5-10 | Cerebral Hemispheres | N | Short-term |
| | Liposomes | CNTF Gene | 4-7 | 5-10 | Cerebral Hemispheres | N | Short-term |
| | Antisense Oligonucleotides | Anti-Huntingtin Gene | 4-7 | 5-10 | Cerebral Hemispheres | Y | Long-term |
| | RNA Interference | Anti-Huntingtin Gene | 4-7 | 5-10 | Cerebral Hemispheres | Y | Long-term |
| Spinocerebellar Ataxia | RNA Interference | Anti-SCA Gene | 3-5 | 0.5-5 | Basal Ganglia, Pons, Cerebellum | Y | Long-term |
| | Antisense Oligonucleotides | Anti-SCA Gene | 3-5 | 0.5-5 | Basal Ganglia, Pons, Cerebellum | Y | Long-term |
| Primary and Secondary Tumours | Novel Chemotherapeutics | Tricyclics | 6-8 | 5-10 | Variable | Y | Short-term |
| | Conventional Chemotherapeutics | Nitrosureas | 6-8 | 5-10 | Variable | Y | Short-term |
| | Immunotoxins | Transferrin-Diphtheria Toxin Constructs | 6-8 | 5-10 | Variable | Y | Short-term |
| | Viruses | Oncolytic HSV | 6-8 | 5-10 | Variable | Y | Short-term |
| | Monoclonal Antibodies | CD44 Antibody | 6-8 | 5-10 | Variable | Y | Short-term |
| Friedreich's Ataxia | Anti-Oxidants | Idabenone | 1-8 | N/K | Variable | Y | Long-term |
| Multiple Sclerosis | Immunomodulators | Interferon | 1-8 | 0.5-10 | Plaque | Y | Long-term |
| | Viral Vectors | Interferon Gene | 1-8 | 0.5-10 | Plaque | N | Short-term |
| | Liposomes | Interferon Gene | 1-8 | 0.5-10 | Plaque | N | Short-term |
| Vasospasm | Growth Factors | MGF | 4-8 | 5-10 | Cerebral Hemispsheres | Y | Short-term |

Fig. 14

FLUID CONNECTOR FOR FLUID DELIVERY APPARATUS

CROSS-REFERENCE TO RELATED APPLICATIONS

This application claims priority to British Patent Application No. 0604952.2, filed in Great Britain on Mar. 13, 2006, and is a National Phase Application of PCT/GB2007/000862, filed on Mar. 12, 2007. The disclosure of the prior applications is hereby incorporated by reference herein in its entirety.

BACKGROUND

1. Field of the Invention

The present invention relates to fluid connectors that are suitable for use in apparatus for delivering fluids, such as drugs, to different parts of the human or animal body. In particular, the invention relates to male and female connector portions suitable for use in a modular drug distribution apparatus for delivering drugs to the brain.

2. Description of Related Art

The drug treatment of a number of neuro-degenerative disorders, hereditary neurological disorders, brain tumours and other diseases of the nervous system are compromised by the presence of the blood brain barrier which prevents the transfer of drugs from the vascular system or cerebrospinal fluid into the brain substance. Examples of drugs which do not adequately cross the blood brain barrier include protein molecules such as neurotrophins, monoclonal antibodies, viral particles for delivery of gene therapy, as well as a number of cytotoxic drugs for the treatment of tumours.

Such drugs may be delivered to the brain by direct infusion into the parenchyma via an indwelling catheter. Upon exiting the catheter the drugs will be dispersed through the brain substance down a concentration gradient (i.e. by diffusion) and/or down a pressure gradient by the process of convection. Large molecules diffuse poorly and so drug delivery into the brain may be best modulated by controlling the rate of drug infusion and thus the degree to which the drug is convected. Convected infusate will carry large molecules such as proteins and viral particles by bulk flow through the interstitial spaces to fill the selected brain volume.

For a number of conditions it is desirable to maximise the volume of drug delivery from a single catheter, as well as to achieve a homogenous concentration of drug throughout the treatment volume. The process by which this is achieved is termed convection enhanced delivery. This may be accomplished, by inserting a catheter with a small external diameter. For example, a catheter of the type described in WO2003/077758 could be used. The drug can then be infused at a flow rate which will preferentially drive the infusate into the interstitial fluid at a maximum tolerated rate that will not cause tissue damage, but also at a rate which will prevent significant reflux along the catheter tissue interface.

For a number of neurological conditions it is desirable to deliver drugs to large volumes of the central nervous system and these would include the treatment of primary or secondary brain tumours, hereditary disorders and conditions such as multiple sclerosis, where any part of the central nervous system may be affected. In these circumstances, it is often desirable to implant multiple catheters into the central nervous system in order to fill the desired volume of tissue with drug. In other conditions it may be desirable to confine a drug to a particular tissue volume so as to minimise its side effects; for example the delivery of GDNF to the striatum to promote its reinnervation with dopaminergic neurons. In these circumstances the desired treatment volume may be filled with a single catheter and the flow rate adjusted to fill the desired volume only.

A variety of implantable drug delivery systems are known and typically comprise a drug pump assembly that can be implanted into the abdomen and one or more flexible catheters that route drug from the pump to the required anatomical site or sites. An example of such an implantable pump is described in US2003/0216714.

For some applications, however, it is not desirable to implant a pump for drug delivery because infrequent repeated treatments are required, such as every few months, which would negate the necessity for long-term implantation of a pump. Additionally for treatments requiring drug delivery to a substantial portion of the central nervous system large volumes of infusate may be required, for example in excess of 50 ml, which would require an excessively large pump reservoir to be implanted which would be inappropriate for infrequent use. Furthermore, some drugs may be unstable when stored at body temperature thus preventing the long term storage of such drugs within implanted reservoirs.

In order to be able to deliver drugs intermittently to the brain using an external pump assembly, the clinician is faced with several problems. The most significant problem is the risk of infection at the site where the tubing connecting the intraparenchymal catheter to the pump exits the skin. Although it is known that tubing for drug delivery into the venous system can be implanted for several months and remain substantially infection free with meticulous aseptic technique, an example of which is the Hickman line, this solution would not be suitable for intermittent drug delivery to the brain because the consequences of infection would be far greater and the period over which intermittent therapy may be given could extend over several years.

An alternative drug delivery solution may be to pass a needle through the skin to a subcutaneous drug infusion port, however, although the skin could be cleaned it cannot be made sterile and there remains a not insignificant risk of the needle carrying bacteria into the subcutaneous infusion port. If the infusion period is continued over many hours or a few days then the risk of infection along the needle track significantly increases. A sharp needle can also carry with it skin debris and this may be carried into the brain, or alternatively block the very fine tubing used for convection enhanced delivery. Furthermore, infusion pressures for convection enhanced delivery may be relatively high because of the very fine bore catheter tubing and extension tubing required. Retaining a transcutaneous needle in an infusion port would in these circumstances also be a concern. Additionally where drug delivery is required to multiple sites within the central nervous system, for example six or more, these problems are similarly multiplied.

SUMMARY

According to a first aspect of the present invention, a male fluid connector portion for tubing having a plurality of lumens is provided, the male fluid connector portion being releasably connectable to a complimentary female fluid connector portion, the male fluid connector portion comprising; a plurality of hollow needles, the hollow needles being arranged such that, when tubing having a plurality of lumens is coupled to the male fluid connector portion, each hollow needle is in fluid communication with one lumen of the tubing; and an alignment guide that allows the hollow needles to be uniquely aligned with the corresponding septum seals of an associated complimentary female fluid connector portion.

The present invention thus relates to a male fluid connector portion that comprises a plurality of hollow needles. Each hollow needle comprises an elongate tube defining a passageway or central channel through which fluid may pass. Each hollow needle may have a proximal end via which it is connected to a fluid supply tube and a distal end (or tip) that may be shaped (e.g. tapered or sheared to a sharp point) to allow it to penetrate the membrane of an associated female connector portion. An aperture may be provided at the tip of the needle and/or on the side of the needle near the tip. Providing a plurality of needles in this manner permits a plurality of separate fluid connections to be made with a complimentary female connector portion. Such a multi-lumen connector enables lengths of multi-lumen tubing to be quickly connected and/or disconnected as required. Such a male fluid connector portion also permits sterile connections to be made and is typically more compact than an arrangement which uses a plurality of single lumen connector portions. A male fluid connector portion of this type is particularly suited for use in the modular fluid delivery apparatus described below and the subject of our co-pending British patent application GB0604929.0, but may also be used in a variety of different medical and non-medical applications.

As outlined above, the male fluid connector portion advantageously comprises an alignment guide to provide alignment of said male fluid connector portion with a complimentary female fluid connector portion when said male and female fluid connector portions are brought into engagement. The alignment guide may comprise a physical alignment feature that ensures connector alignment. For example, the alignment guide may comprise one or more protruding alignment prongs, or complimentary alignment slots and/or grooves etc. The alignment guide may also be provided by the relative positioning of the needles themselves. Alternatively, the alignment guide may comprise one or more visible markings to aid proper connector alignment. The alignment guide is thus arranged so that the hollow needles of the male fluid connector portion are uniquely aligned with the respective resilient membranes of the female fluid connector portion when the portions are connected together. This ensures that fluid communication is separately established between the required lumens of the tubing attached to the male and female fluid connector portions.

Conveniently, the male fluid connector portion comprises a substantially cylindrical portion having a screw thread for engaging the complementary screw thread of a female connector. Advantageously, the substantially cylindrical portion of the male fluid connector portion is rotatable relative to the remainder of the male fluid connector portion. The cylindrical portion may thus be a rotatable cylindrical portion having a screw thread formed on its inner surface such that, when the screw thread of the cylindrical portion engages the complementary screw thread of a female connector, rotation of the rotatable cylindrical portion acts to bring the male and female connectors into engagement. In this manner, the male and female fluid connector portions may be connected using a simple screw action.

Advantageously, the distal tip of each of said plurality of hollow needles is located within the volume enclosed by the cylindrical portion. In other words, the cylindrical portion encases the hollow needles thereby preventing inadvertent damage to such needles prior to, or during, connection.

Preferably, the longitudinal axes of each of said plurality of hollow needles are substantially parallel to the longitudinal axis of said cylindrical portion. If the male fluid connector portion comprises alignment guide means having one or more protruding alignment prongs, the longitudinal axis of each protruding alignment prong may also be substantially parallel to the longitudinal axis of said cylindrical portion. Furthermore, one of said one or more alignment prongs may conveniently be substantially co-axially aligned with said cylindrical portion.

Advantageously, the distal end of each alignment prong protrudes beyond the volume enclosed by the cylindrical portion. In other words, the distal end of the alignment prongs may be arranged to extend beyond the casing of the male fluid connector portion. Preferably, at least two alignment prongs are provided to allow the orientation of the male and female connector portions to be uniquely aligned. This arrangement permits the alignment prong(s) to enter the recesses of the corresponding female fluid connector portion, thereby angularly and axially aligning the male and female portions, before the hollow needles are brought into contact with the resilient membranes of the female connector portion. As described below, this prevents lateral forces being exerted on the hollow needles during the connection process.

The plurality of hollow needles and the alignment prongs are preferably arranged in a first pattern. For example, they may be evenly angularly displaced a certain radial distance from the longitudinal axis of the cylindrical portion. Any other configuration is possible as required. As outlined below, the female fluid connector portion is preferably arranged to have series of recesses and resilient membranes (septum seals) that adopt a pattern that is complimentary to said first pattern.

A wide variety of different material(s) may be used to form the hollow needles. The hollow needles may be formed from a combination of different material and may also comprise one or more coatings on the outer and/or inner surfaces as required. For example, the hollow needles may conveniently comprise at least one of silica, stainless steel, tungsten, tungsten carbide, titanium, titanium carbide, ceramic and plastic. The hollow needles may conveniently each comprise a hollow core in which a fluid carrying tube (e.g. from an associated length of tubing) can be located. In a preferred embodiment described below, the hollow needles are formed from stainless steel and contain an inner silica core through which fluid can be passed. Silica is advantageous because it is not susceptible to the build up of foreign matter (e.g. bacteria).

The male fluid connector portion may comprise as many hollow needles as required. If a multi-lumen tube is terminated at said male fluid connector portion, the connector portion may comprise sufficient hollow needles to establish a separate fluidic link with each of said lumens. The male fluid connector portion may be arranged to retain a maximum number of needles, but when used it may be arranged to contain fewer needles than said maximum if required. The male fluid connector portion preferable comprises at least three hollow needles, at least four hollow needles, at least five hollow needles, at least six hollow needles, at least seven hollow needles, at least eight hollow needles, at least ten hollow needles, or at least fifteen hollow needles.

Advantageously, the male fluid connector portion is arranged to receive tubing comprising a plurality of lumens, wherein fluid communication is provided between each lumen and an associated one of said plurality of hollow needles. The male connector portion may also be attached (e.g. permanently) to a length of tubing having a plurality of lumens, each lumen being in fluid communication with one of said hollow needles. The tubing may, for example, comprise a sheath containing a plurality of tubes. In such a case, the sheath may be cut back and the proximal end of a hollow needle may be attached to each tube. The sheath may also be arranged to have a portion moulded or attached to its end which prevents the tubing being withdrawn from the connector. The sheath may also be toughened as required, although the tubing is preferably flexible. A length of tubing may also be provided having an inner multi-lumen bundle (e.g. a plurality of separate tubes or a multi-lumen tube) that is slideable within an outer protective sheath. The inner multi-lumen bundle may then be inserted into, and withdrawn from, the outer sheath even after the outer sheath has been implanted in the body. This would allow the inner multi-lumen bundle to be easily replaced (e.g. if a lumen became blocked or started leaking).

According to a second aspect of the invention, a female fluid connector portion for tubing having a plurality of lumens is provided, the female fluid connector portion being releasably connectable to a complimentary male fluid connector portion, the female fluid connector portion comprising; a plurality of chambers, each chamber comprising a septum seal through which a hollow needle can be passed, wherein, when tubing having a plurality of lumens is coupled to the female connector portion, each lumen is in fluid communication with one of said chambers; and an alignment guide that allows the septum seals to be uniquely aligned with the corresponding hollow needles of an associated complimentary male fluid connector portion.

The present invention thus also provides a female fluid connector portion that comprises a plurality of chambers, each chamber comprising a resilient membrane through which a hollow needle can be passed. Such a female connector portion may be connected to a male connector portion of the type described above. Each chamber of the female fluid connector portion may be in fluid communication with the lumen of an outlet tube and the resilient membrane (i.e. septum seal) is arranged to provide a resealable wall through which the hollow needle of a male connector can be passed thereby establishing fluid communication between the core of the hollow needle and the chamber.

As outlined above the female fluid connector portion preferably comprises an alignment guide. The alignment guide or alignment guide means may be arranged to provide alignment of said female fluid connector portion with a complimentary male fluid connector portion when said female and male fluid connector portions are brought into engagement. The alignment guide may be a physical feature; for example, the alignment guide of the female fluid connector portion comprises at least one elongate recess for receiving an alignment prong of an associated male fluid connector portion. The alignment guide may alternatively comprise at least one visible marking. Such guide means are described in more detail above in connection with the male connector portion. It should also be noted that the alignment guide of the male connector portion may comprise a recess or recesses for receiving the alignment prong(s) of a female connector; the definition of "male" and "female" connector portions is, herein, arbitrarily based only on the presence or absence of the hollow needles.

Advantageously, the female fluid connector portion comprises a second cylindrical portion having a screw thread for engaging the complementary screw read of a male connector. If alignment guide means are provided that comprise at least one elongate recess for receiving an alignment prong of an associated male fluid connector portion, the longitudinal axis of said at least one elongate recess is preferably substantially parallel to the longitudinal axis of said second cylindrical portion. Conveniently, when the rotatable screw thread of a complimentary male fluid connector portion engages and is rotated relative to the screw thread portion of the female connector, hollow needles of the associated male connector portion are translated only in a direction that is substantially perpendicular to the plane of said resilient membranes.

In this manner, any substantial lateral movement of the hollow needles of the associated male fluid connector portion is prevented; this ensures such needles do not shear, snap or bend when the connection is made.

Conveniently, the female fluid connector portion comprises an outer casing having an annular end portion comprising a plurality of apertures through which the septum seal of each chamber can be accessed. Advantageously, the resilient membrane of each chamber is provided by a common annular, resilient, member retained against the inner surface of annular end portion. Such a common annular, resilient, member may comprise one or more apertures aligned with the recess or recesses of the alignment guide.

Advantageously, the female fluid connector portion is arranged to receive tubing comprising a plurality of lumens, wherein fluid communication is provided between each lumen and an associated one of said chambers. The number of lumens of the tubing may be equal to the number of chambers. The female fluid connector portion may be attached to a length of tubing having a plurality of lumens, each lumen being in fluid communication with one of said chambers Preferably, the septum seal or resilient membrane of each chamber comprises rubberised material. Advantageously, the septum is arranged to provide a fluidic seal that prevent egress of fluid through said membrane when no needle is inserted therethrough. In this manner a self sealing female connector portion is provided.

In accordance with the present invention, a connector may be provided which comprises a male fluid connector portion and a female fluid connector portion of the type described above. Also, according to a third aspect of the invention, a connector for tubing having a plurality of lumens is provided, the connector comprising a male portion comprising a plurality of hollow needles and a female portion comprising a plurality of septum seals through which said plurality of hollow needles can be passed, wherein the connector comprises an alignment guide for uniquely aligning the hollow needles of the male portion with defined septum seals of the female fluid connector when the male fluid connector portion and the complementary female fluid connector portion are brought into engagement. The connector may be a medical connector; for example, it may be suitable for implantation as part of the modular fluid delivery apparatus described below.

Furthermore, a connector apparatus kit may be provided that comprises at least one of a male fluid connector portion, a female fluid connector portion and a connector of the type described above. The kit may further include at least one of a length of tubing, a catheter, a fluid pump and implantable housing for encasing said connector part.

The invention will now be described, by way of example only, with reference to the accompanying drawings.

DETAILED DESCRIBED OF EMBODIMENTS

Figure 1:
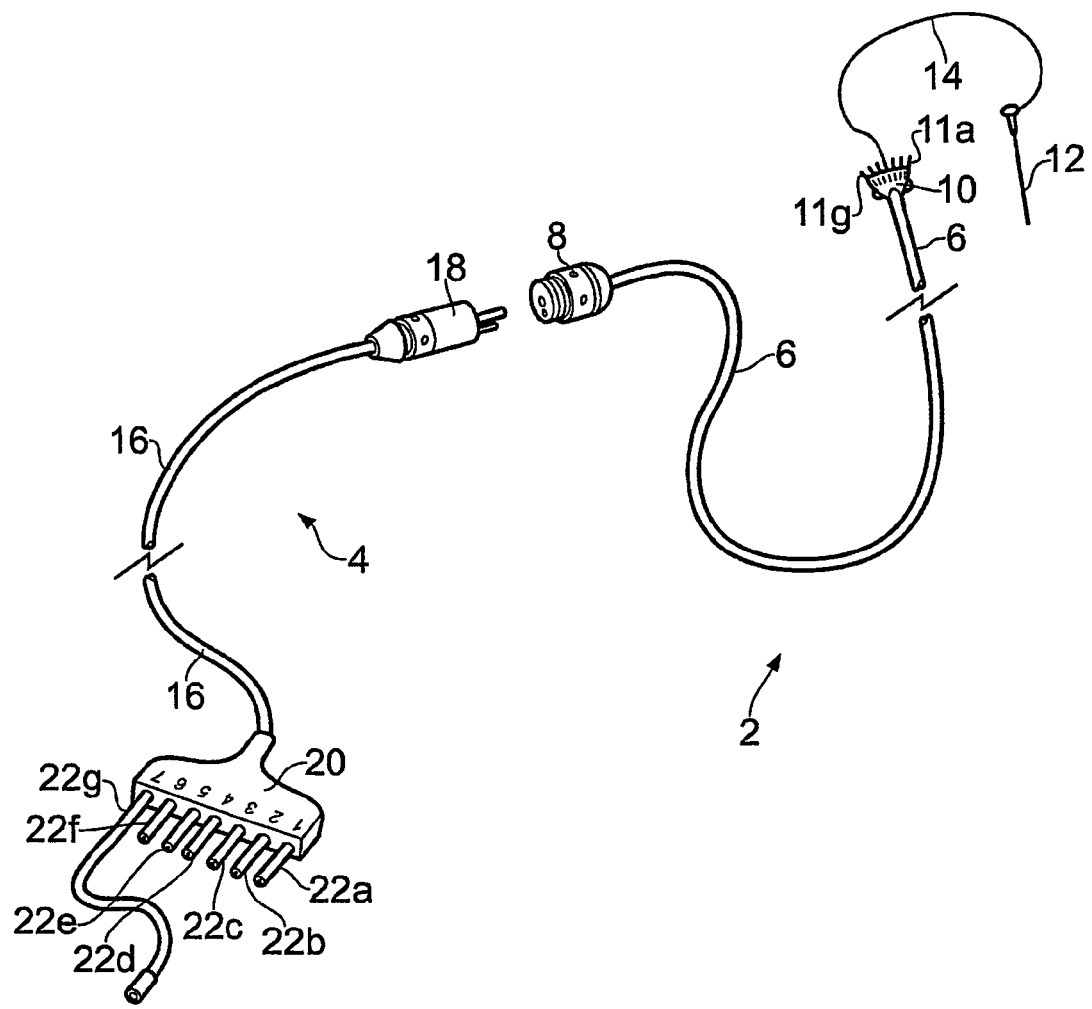
FIG. 1 illustrates modular drug delivery apparatus.

Referring to FIG. 1, apparatus for delivering a drug to the brain of a subject is shown. The apparatus is modular and comprises a first part 2 and a second part 4.

The first part 2 of the apparatus comprises a first seven-lumen tube 6 that couples a female seven-lumen connector portion 8 to an implantable fluidic router 10. The fluidic router 10 has seven outputs 11a-11g. Each of the outputs 11 is connected to an associated catheter 12 via a length of single lumen tubing 14 (noting that only one such catheter is shown in FIG. 1). The second part of the apparatus comprises a second seven-lumen tube 16 that couples a male seven-lumen connector portion 18 to an external fluidic router 20. The external fluidic router 20 has seven inputs 22a-22g, each input being suitable for receiving fluid under pressure from an associated pump assembly.

The male seven-lumen connector portion 18 of the second part is arranged to mate with the female seven-lumen connector portion 8 of the first part so that fluid communication can be established between respective lumens of the first seven-lumen tube 6 and the second seven-lumen tube 16. In this manner, fluid communication is separately established between each of the seven router inputs 22 and an associated catheter 12.

Figure 3:
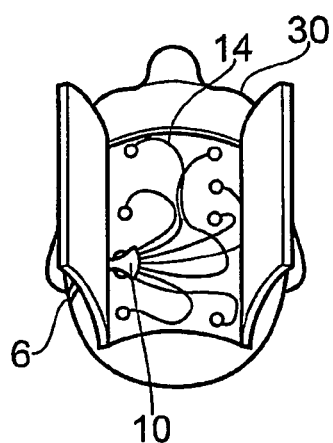
FIG. 3 gives an expanded view of the head of the subject of FIG. 2.
Figure 2:
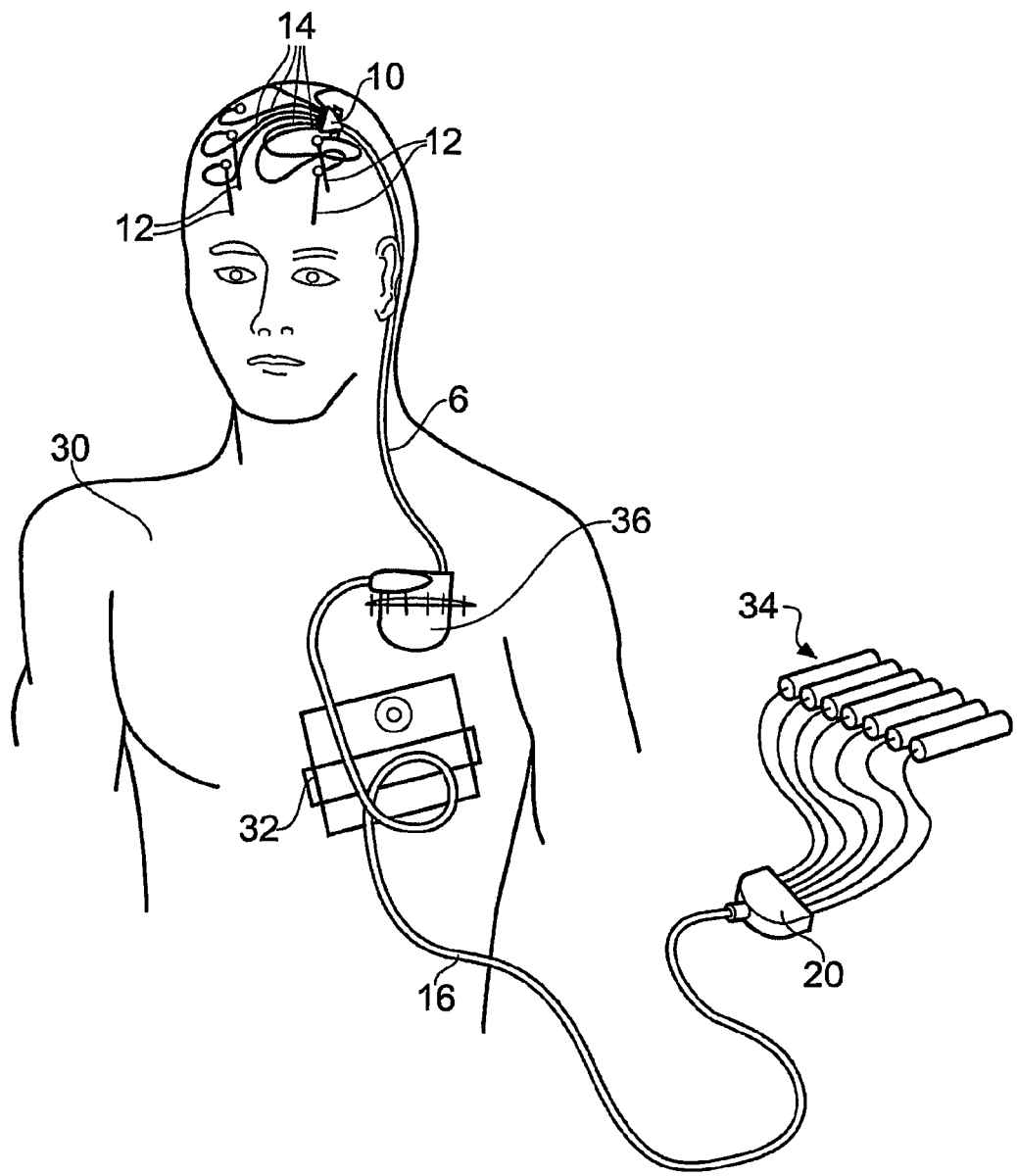
FIG. 2 illustrates the apparatus of FIG. 1 implanted in a subject.

Referring to FIGS. 2 and 3, the apparatus of FIG. 1 is illustrated when arranged to deliver a drug to the brain of a subject 30. In particular FIG. 2 shows the upper body of a subject and FIG. 3 gives an expanded view of the top of the head of that subject.

The first part 2 of the apparatus is fully implanted within the subject 30 and will typically remain in situ for the duration of a course of treatment (which may include multiple periods of drug delivery). Implantation of the first part 2 of the apparatus will necessarily involve a complex surgical procedure in which the tips of the interparenchymal catheters 12 are carefully positioned at the required locations within the brain. This procedure will also require implantation of the various lengths of single lumen tubing 14, the mounting of the implantable fluidic router 10 to the skull and sub-cutaneous tunneling of the first multi-lumen tube 6 from the scalp to the chest region.

A detailed view of the implantable fluidic router 10, the single lumen tubing 14 and the proximal ends of the catheters 12 after surgical implantation in the head of the subject is given in FIG. 3. The arrangement of the seven catheters shown in FIG. 3 allows delivery of a drug to the entire brain. Two catheters ($F_1$ and $F_2$) are inserted to deliver drug to the left and right frontal lobes. A further pair of catheters ($P_1$ and $P_2$) are inserted to permit delivery to the left and right parieto-occipital lobes. Two more catheters ($T_1$ and $T_2$) are inserted so as to delivery drugs to the left and right tempo-occipital lobes and a catheter ($P_s$) is inserted into the pons to allow drugs to be driven down into the cerebellum through the white matter tracks.

The male seven-lumen connector portion 18 of the second part 4 of the apparatus is connected to the female seven-lumen connector portion 8 of the first part 2 of the apparatus. The connector is retained in a housing 36 that may be anchored to the subject (e.g. by a suture). The second length of seven-lumen tubing is passed through an incision 32 in the thorax (e.g. in the chest) and each input 22 of the external fluidic router 20 is connected to a fluidic output of an external pump assembly 34. As the tubing 16 enters the body at an anatomical location which is a significant distance from the central nervous system (CNS), the possibility of any infection at the aperture reaching the CNS is minimised.

Once implanted, the apparatus provides a separate fluidic pathway from each of the seven outputs of the pump assembly 4 to an associated one of the seven catheters 18. This allows fluid to be routed to any one of the seven catheters as required. The drug delivery profile (e.g. drug concentration, fluidic pressure, flow rate etc) may thus be set as required by a clinician by suitably programming the external pump assembly 34. The pump assembly 34 may be arranged to pump fluid to the catheters in any desired manner; for example, drug may be delivered sequentially or simultaneously to the different catheters.

As shown in FIG. 2, the pump assembly comprises seven different outputs, each of which is connected to one of the router inputs 22. The provision of such an external pump assembly allows the administration of drugs that have short half lives and/or which must be stored at low temperatures and/or which must be delivered in large volumes. External pumps also have the advantage of being readily accessibly (compared with implanted pumps) in case of failure or malfunction.

The modular apparatus described herein allows the second part 4 of the apparatus to be disconnected from the first part 2 of the apparatus when drug delivery is no longer required. The removal of the second part 4 involves a relatively simple surgical procedure in which the chest incision is re-opened and the first and second parts of the apparatus are disconnected. Subsequently, when an additional dosage of drug is to be delivered, the second part 4 can be reconnected to the first part 2 by reversing such a procedure.

The apparatus thus allows an initial, rather complex, surgical procedure to be performed in which the first and second parts of the apparatus is implanted as described above. A first dose of the necessary drugs can then be given, after which a relatively simple surgical procedure can be performed to remove the second part of the apparatus from the subject. After the second part of the apparatus is removed, the subject may be temporarily discharged from medical care and, because the remaining first part of the apparatus is fully implanted within the body, there will be no tubes exiting the body that need to be kept sterile to prevent infection. After a suitable period of time, the subject may undergo a further, again relatively simple, surgical procedure that involves making an incision in the chest and reconnecting a second part of the apparatus to the first part of the apparatus. This may be followed by the administration of a further dose of the required drug(s) and subsequent surgical removal of the second part of the apparatus. This may be repeated as many times, and as frequently, as required. If the treatment is completely successful, the first part of the apparatus may also be removed from the subject.

Figure 4:
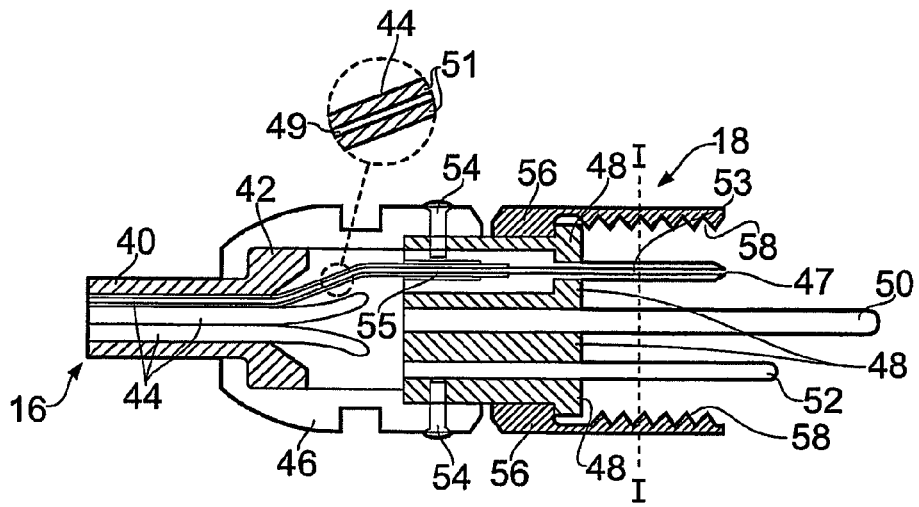
FIG. 4 is a sectional view along a male connector portion.
Figure 5:
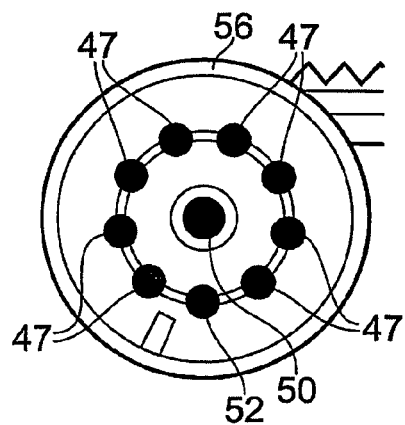
FIG. 5 is a cross-sectional view of the male connector portion of FIG. 4.
Figure 6:
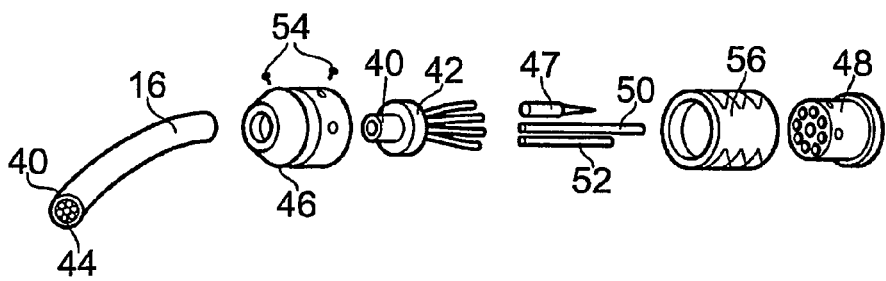
FIG. 6 is an exploded view of a connector portion of the type shown in FIGS. 4 and 5.

Referring to FIGS. 4 to 6, the structure of the male seven-lumen connector portion 18 and the associated seven-lumen tubing 16 will now be described.

The tubing 16 received by the connector portion 18 comprises an outer cable sheath 40 within which a bundle of seven single lumen tubes 44 are retained. The cable sheath also comprises a radially extending end portion 42. The male connector portion 18 comprises an end cap portion 46 having an aperture through which the tubing 16 is passed. The radially extending end portion 42 of the cable sheath 40 is arranged to prevent the cable being drawn back though the aperture of the end cap portion 46. The seven single lumen tubes 44 fan out within the end cap portion 46 and are each routed to a hollow needle 47. It should be noted that, for clarity, only a single needle is illustrated in FIGS. 4 and 6.

Each hollow needle 47 is formed of a resilient, preferably rigid, material. The hollow needles 47 may thus be formed from a metal or any suitable material; for example, the hollow needles may comprise stainless steel, tungsten, tungsten carbide, titanium, titanium carbide, plastic etc. As shown in the inset of FIG. 4, each of the single lumen tubes 44 comprises an inner fused silica tube 49 (i.e. defining the lumen) that is surrounded by protective plastic cladding 51. To connect the single lumen tube 44 to the needle 47, the cladding 51 is removed from a region at the distal end of each tube 44. Each needle 47 is arranged such that the inner fused silica tube (absent any cladding) can pass through the hollow core 53 that runs to the distal end (or tip) of the needle and also comprises, at its proximal end, an aperture 55 for receiving the silica tube 49 with cladding 51 attached thereto. The tubing 44 (with the cladding stripped back from its end) can thus be inserted into the needle until the cladding fills the aperture 55; the exposed length of silica core at the end of the tube 44 can also be made sufficiently long to extend the tip of the hollow needle. Once inserted, the tubing may be bonded to the needle 47 using adhesive or any other suitable attachment means. In this manner a fluidic seal can be readily established.

The male connector portion also comprises a retaining block 48 having a central aperture and eight further radial apertures that are angularly spaced about the central aperture. A first alignment prong 50 is retained within the central aperture of the retaining block 48 and a second alignment prong 52 is retained within one of the radial apertures of the retaining block 48. The seven needles 47 are retained in the remaining radial apertures of the retaining block 48. The needles 47 and alignment prongs 50 and 52 may be secured to the retaining block 48 by any appropriate means (e.g. by adhesive, welding, bonding or with appropriate fixings etc). Screws 54 are also provided to fix the end cap portion 46 to the retaining block 48.

A cylindrical casing portion 56 is also provided which is rotatably mounted to the retaining block 48. The cylindrical casing portion 56 has an internal screw thread 58 that mates with a complimentary screw thread of the female connector portion. The connector portion 18 is arranged such that the seven protruding needles 47 and the two alignment prongs 50 and 52 extend in directions that are substantially parallel to the central axis of the cylindrical casing portion 56. The needles 47 are arranged to extend no further than the end of the cylindrical casing portion 56, thereby reducing the possibility of the needles being accidentally broken or damaged. The first and second alignment prongs 50 and 52 are arranged to extend beyond the cylindrical casing 56 and the first (central) alignment prong 50 is arranged to extend further from the connector portion than the second alignment prong. The radial arrangement of the first and second alignment prongs and the associated needles are shown in detail in FIG. 5 which is a sectional view along the line I-I of FIG. 4.

Figure 7:
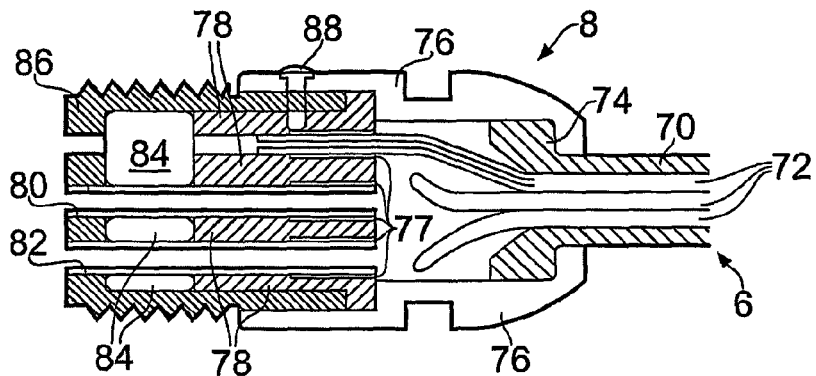
FIG. 7 is a sectional view along a female connector portion.
Figure 8:
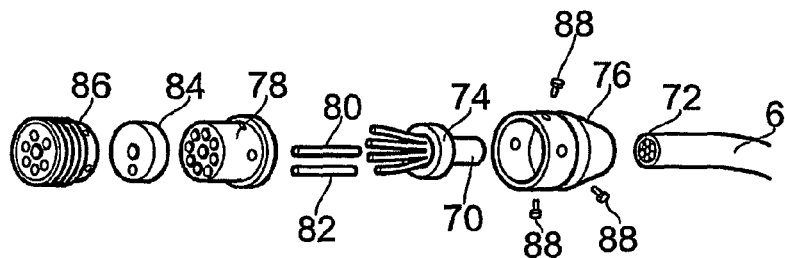
FIG. 8 is an exploded view of a connector portion of the type shown in FIG. 7.

Referring to FIGS. 7 and 8, the structure of a female seven-lumen connector portion 8 which is complimentary to the above described male connector portion 18 is shown.

The tubing 6 received by the female connector portion 8 comprises an outer cable sheath 70 within which a bundle of seven single lumen tubes 72 are retained. The cable sheath also comprises a radially extending end portion 74.

The female connector portion 8 comprises an end cap 76 having an aperture through which the tubing 6 is passed. The radially extending end portion 74 of the cable sheath 70 is arranged to prevent the cable being withdrawn though the aperture of the end cap 76. The seven single lumen tubes 72 are arranged to fan out within the end cap portion 76.

A cavity block 78 is also provided having a central aperture and eight further radial apertures that are angularly spaced about the central aperture. The relative positions of the nine apertures of the cavity block 78 are matched to the positions of the apertures of the retaining block 48 of the complimentary male connector portion 18. A first tubular portion 80 and a second tubular portion 82 are located within the central aperture of the cavity block and a radial aperture of the cavity block 78 respectively. The other seven radial apertures each receive an end of an single lumen tube 72. The ends of the single lumen tubes 72 and the first and second tubular portions 80 and 82 are retained within the apertures of the cavity block 78 by an appropriate fixing means 77 (e.g. using adhesive, welding, bonding or with appropriate fixings etc). The fixing means 77 also provides a fluidic seal between the single lumen tube 72 and the associated aperture of the cavity block.

Screws 88 are passed through the end cap portion 76 and a threaded end portion 86 in to the cavity block 78 thereby retaining such components in a fixed spaced relation. A annular rubber bung 84 is also retained within the threaded end portion 86 and is forced into engagement with the end of the cavity block 78. The rubber bung 84 has two apertures which are aligned such that the first and second tubular portions 80 and 82 pass therethrough. The threaded end portion 86 has an arrangement of apertures that match that of the cavity block 78 and an outer thread suitable for engaging the thread of the male connector portion 18.

The assembled female connector portion 8 thus comprises seven sealed apertures (i.e. sealed by the rubber bung 84) for receiving a needle and two apertures for receiving the alignment prongs of a complimentary male connector portion. The apertures for receiving the alignment prongs are arranged to have a larger diameter than the sealed apertures. A needle inserted into one of sealed apertures will pass through the rubber bung 84 and enter the associated cavity of the cavity block. In this manner, fluid communication can be established between the needle and the associated single lumen tube retained by that cavity. In the absence of such a needle, the apertures are sealed by the rubber bung 84 thus preventing fluid passage into, or out of, the associated tubes.

Figure 9:
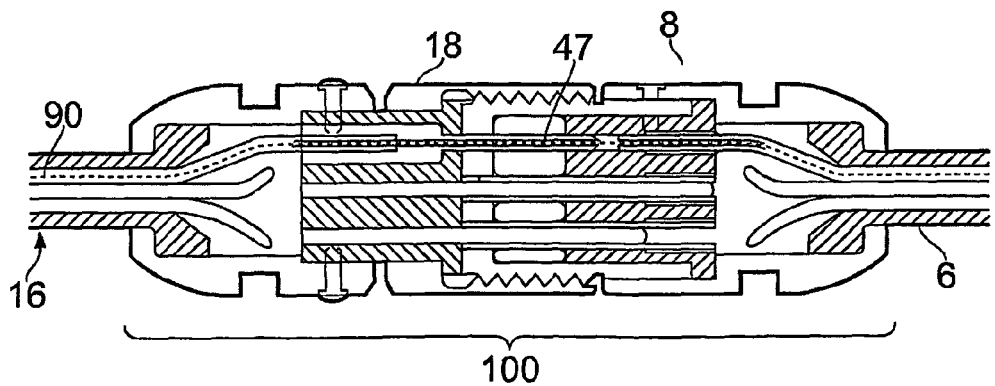
FIG. 9 illustrates the male connector portion of FIGS. 4 to 6 connected to the female connector portion of FIGS. 7 and 8.

Referring to FIG. 9, a male connector portion 18 of the type described with reference to FIGS. 4 to 6 is shown when mated with a female connector portion 8 of the type described with reference to FIGS. 7 and 8 thus forming a connector 100. Once the female connector portion 8 is mated with the male connector portion 18, seven separate fluidic connections are established between the seven lumens of the first and second seven-lumen tubes 6 and 16. The dashed line 90 of FIG. 9 illustrates the flow path from one lumen of the second seven-lumen tube 16, through the hollow needle 47 and into an associated lumen of the first seven-lumen tube 6.

A male connector portion 18 may be connected to a female connector portion 8 in the following manner. Firstly, the central alignment prong 50 of the male connector portion is located in the central first tubular portion 80 of the female connected. The male connector portion is then rotated relative to the female connector portion until the second alignment prong 52 enters the second tubular portion 82. At this point, the cylindrical casing 56 of the male connector portion 18 is rotated such that its internal screw thread 58 engages the complimentary thread of the threaded end portion 86 of the female connector portion 8. Further rotation of the cylindrical casing 56 of the male connector portion 18 urges the needles 47 through the rubber bung 84 and into the cavity of the cavity block. It should be noted that once the alignment prongs are aligned with the tubular portions, tightening the screw thread causes the needles to move in a direction that is substantially parallel to the longitudinal axes of the male and female connector portions. In other words, the needles are forced through the rubber bung from a direction substantially perpendicular to that bung; i.e. without any significant lateral movement which might cause such needles to deform or snap.

Unscrewing the cylindrical casing 56 from the threaded end portion 86 of the female connector portion 8 causes retraction of the needles 47 through the rubber bung, again without any substantial later movement. Once disconnected, the rubber bung 84 again acts to seal each cavity of the cavity block 78 thereby preventing egress of fluid from the first seven-lumen tube 6.

Figure 10:
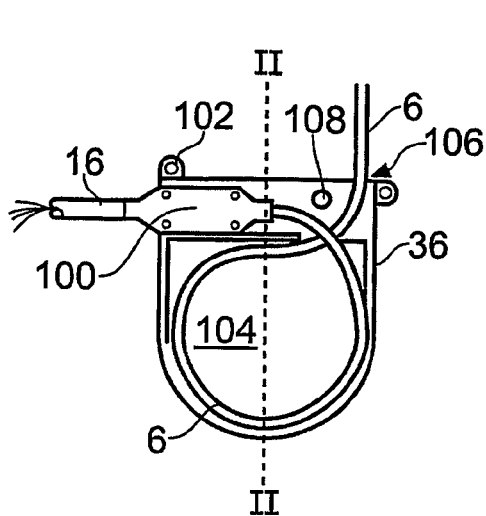
FIG. 10 shows a cut away plan view of an implantable housing for retaining a connector.
Figure 11:
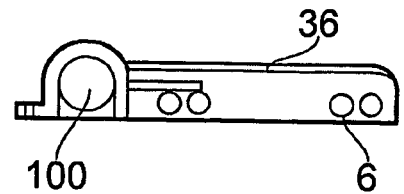
FIG. 11 is a cross-sectional view of the housing of FIG. 10.
Figure 12:
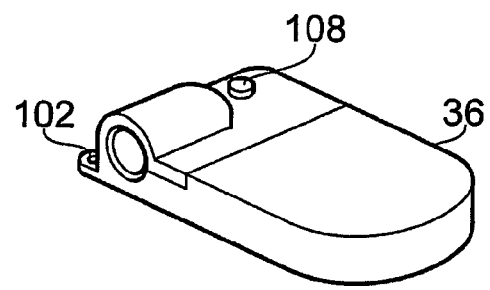
FIG. 12 shows the external shape of the housing of FIGS. 10 and 11.

Referring now to FIGS. 10 to 12, a housing 36 of the type described above with reference to FIG. 2 is shown. In particular, FIG. 10 shows a plan view through the housing 36 with a connector 100 retained therein whilst FIG. 11 gives a cross-sectional view along the line II-II of FIG. 10. FIG. 12 provides a further view of the housing, absent a retained connector.

The housing 36 is designed to retain and enclose a connector 100 of the type described above. The connector provides fluidic connection between the lumens of the first seven lumen tube 6 and the second seven lumen tube 16. The housing also comprises attachment flanges 102 for securing the housing 36 to the human or animal body in which it is implanted using, for example, sutures.

In order to allow for movement of the subject after implantation of the drug delivery apparatus, the housing also comprises an internal cavity 104 in which a loose coil of a length of the first tubing 6 is located. The tubing 6 is arranged to exit the housing 36 via an aperture 106. Providing such a coil enables the subject to move freely; the coil of tubing extending and retracting as required with such movement. To allow easy connection and disconnection of the first and second parts of the drug delivery apparatus, the housing may comprise a flip top that is secured to the base with a screw 108. Undoing the screw 108 allow access to the internal cavity of the housing and hence to the connector 100.

Figure 13:
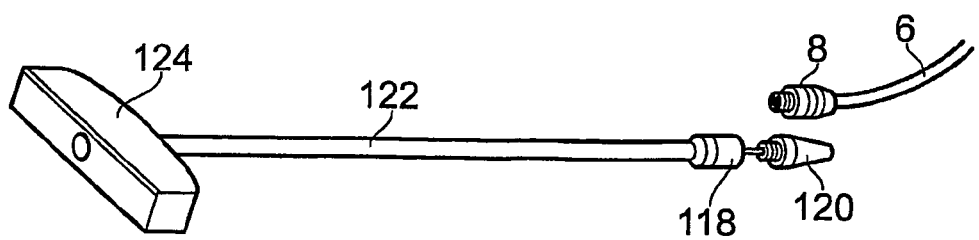
FIG. 13 shows introducer apparatus, and FIG. 14 lists various drugs which could be delivered using the apparatus of FIGS. 1 to 12.

Referring now to FIG. 13, surgical introducer apparatus is shown for subcutaneously tunnelling the first seven-lumen tube 6 from the scalp to the chest region. The introducer apparatus comprises a length of deformable flexible material 122 having a handle 124 at its proximal end and a pseudo-male connector portion 118 attached to its distal end.

The pseudo-male connector portion 118 is analogous to the male connector portion 18 described with reference to FIGS. 4-6 above, except that it does not include the needles 47 and is not connected to the seven-lumen tube 16. The pseudo-male connector portion 118 thus includes the rotatable cylindrical portion and the alignment prongs which allows it to be physically attached to a female connector portion 8 of the type described with reference to FIGS. 7 and 8. However, attaching the female connector portion 8 to the pseudo-male connector portion 118 does not break the fluidic seal provided by the rubber bung of the female connector portion 8.

A pseudo-female connector portion 120 may also be provided. The pseudo-female connector portion 120 has a screw thread that will engage the pseudo-male connector portion 118 an apertures for receiving the alignment prongs of the pseudo-male connector portion 118. The distal end of the pseudo-male connector portion 118 is cone shaped.

The introducer apparatus is used in the following manner. Firstly, incisions are made in the scalp of the subject allowing the catheters 12 and the implantable fluidic router 10 etc to be implanted as required. An incision is then made in the chest of the subject. The pseudo-female connector portion 120 is attached to the pseudo-male connector portion 118 of the introducer apparatus. The introducer is then inserted in the chest incision and pushed upwardly towards the scalp incision. Once the distal end of the introducer apparatus exits the subject via the scalp incision, the pseudo-female connector portion 120 is detached from the pseudo-male connector portion 118. The female connector portion 8 of the first part 2 of the drug delivery apparatus is then connected to the pseudo-male connector portion 118 and the introducer apparatus is withdrawn back through the chest incision. This withdrawal pulls the female connector portion 8 and the attached first seven lumen tubing 6 from the scalp to the chest. The pseudo-male connector portion 118 can then be disconnected from the female connector portion 8 and the male and female connectors may be connected to form a connector 100 which can be located in a housing 36.

Once implanted, the modular apparatus described above can be used for a wide variety of different treatments. Referring to FIG. 14, a number of potential applications for convection enhanced delivery to the brain are provided. In particular, the type of agent and the number of 0.2 mm outer diameter catheters required to deliver such an agent are shown. In certain circumstances, the delivery regimen may require continuous delivery whilst other treatments may require pulsed (bolus) delivery. It should be noted that the list of FIG. 14 is by no means exhaustive. The skilled person would appreciate the numerous applications in which apparatus of the type described above could be used.

The above apparatus specifically describes the delivery of drugs to the brain via seven catheters. It should be again noted that neither of these features are essential elements of the invention. Despite being particularly suited to delivering drugs to the central nervous system, the apparatus described above could be used to deliver any type of fluid to any part of the human or animal body. Furthermore, the apparatus could comprise any number of fluidic pathways from an external pump to internally implanted catheters.

The invention claimed is:

1. A male fluid connector portion for tubing having a plurality of lumens, the male fluid connector portion being releasably connectable to a complementary female fluid connector portion, the male fluid connector portion being for medical use, the male fluid connector portion comprising:
   a plurality of hollow needles, a distal end of each of the plurality of hollow needles including a sharp point that can pass through a septum seal of a complementary female fluid connector portion, the plurality of hollow needles being arranged such that, when tubing having a plurality of lumens is coupled to the male fluid connector portion, a proximal end of each of the plurality of hollow needles is in fluid communication with one lumen of the tubing; and an alignment guide that allows the plurality of hollow needles to be uniquely aligned with the corresponding septum seals of an associated complementary female fluid connector portion.

2. A male fluid connector portion according to claim 1 wherein the alignment guide comprises one or more protruding alignment prongs.

3. A male fluid connector portion according to claim 1 wherein the alignment guide comprises one or more visible markings.

4. A male fluid connector portion according to claim 1 comprising a substantially cylindrical portion having a screw thread for engaging a complementary screw thread of a complementary female fluid connector portion.

5. A male fluid connector portion according to claim 4 wherein the substantially cylindrical portion is a rotatable cylindrical portion having a screw thread formed on its inner surface such that, when the screw thread of the cylindrical portion engages the complementary screw thread of a female connector, rotation of the rotatable cylindrical portion acts to bring the male and female connectors into engagement.

6. A male fluid connector portion according to claim 4 wherein the distal end of each of the plurality of hollow needles is located within a volume enclosed by the cylindrical portion.

7. A male fluid connector portion according to claim 4 wherein a longitudinal axes of each of the plurality of hollow needles are substantially parallel to a longitudinal axis of the cylindrical portion.

8. A male fluid connector portion according to claim 4, wherein the alignment guide has one or more protruding alignment prongs, and a longitudinal axis of each protruding alignment prong is substantially parallel to the longitudinal axis of the cylindrical portion.

9. A male fluid connector portion according to claim 8 wherein one of the one or more alignment prongs is substantially co-axially aligned with the cylindrical portion.

10. A male fluid connector portion according to claim 8 wherein the distal end of each alignment prong protrudes beyond the volume enclosed by the cylindrical portion.

11. A male fluid connector portion according to claim 8 wherein the plurality of hollow needles and the alignment prongs are arranged in a first pattern.

12. A male fluid connector portion according to claim 1 wherein the plurality of hollow needles includes at least one of silica, stainless steel, tungsten, tungsten carbide, Titanium, Titanium carbide, ceramic and plastic.

13. A male fluid connector portion according to claim 12 wherein each hollow needle has a hollow core in which a tube can be located.

14. A male fluid connector portion according to claim 1 comprising at least five hollow needles.

15. A male fluid connector portion according to claim 1 wherein each hollow needle has an aperture in the side and/or distal end thereof.

16. A male fluid connector portion according to claim 1, wherein the male fluid connector portion is attached to a length of tubing having a plurality of lumens, each lumen being in fluid communication with one of said hollow needles.

17. A connector comprising a male fluid connector portion according to claim 1 and a female fluid connector portion for tubing having a plurality of lumens, the female fluid connector portion being releasably connectable to the male fluid connector portion, wherein the female fluid connector portion includes:

a plurality of chambers, each chamber including a septum seal through which a hollow needle can be passed, wherein, when tubing having a plurality of lumens is coupled to the female connector portion, each lumen is in fluid communication with one of the plurality of chambers; and an alignment guide that allows the septum seals to be uniquely aligned with the corresponding hollow needles of the male fluid connector portion.

18. A connector according to claim 17 for medical use.

19. A connector kit comprising:

at least one of a male fluid connector portion according to claim 1, or a female fluid connector portion for tubing having a plurality of lumens, the female fluid connector portion being releasably connectable to the male fluid connector portion, the female fluid connector portion being for medical use, the female fluid connector portion including a plurality of chambers, each of the plurality of chambers including a septum seal through which a hollow needle can be passed, and which prevents the egress of fluid when no needle is inserted therethrough, wherein, when tubing having a plurality of lumens is coupled to the female connector portion, each lumen is in fluid communication with one of said chambers, and an alignment guide that allows the septum seals to be uniquely aligned with the corresponding hollow needles of the male fluid connector portion, or a medical fluid connector for tubing having a plurality of lumens, the connector including a male portion including a plurality of hollow needles, a distal end of each of the plurality of hollow needles including a sharp point, and a female portion including a plurality of septum seals through which said plurality of hollow needles can be passed and which prevents the egress of fluid when no needle is inserted through, wherein the connector includes an alignment guide for uniquely aligning the hollow needles of the male portion with defined septum seals of the female portion when the male female portion are brought into engagement, the kit also comprising at least one of a length of tubing, a catheter, a fluid pump and an implantable housing for encasing said connector part.

20. A female fluid connector portion for tubing having a plurality of lumens, the female fluid connector portion being releasably connectable to a male fluid connector portion, the female fluid connector portion being for medical use, the female fluid connector portion comprising:

a plurality of chambers, each of the plurality of chambers including a septum seal through which a hollow needle can be passed, and which prevents the egress of fluid when no needle is inserted therethrough, wherein, when tubing having a plurality of lumens is coupled to the female connector portion, each lumen is in fluid communication with one of said chambers; and an alignment guide that allows the septum seals to be uniquely aligned with the corresponding hollow needles of the male fluid connector portion.

21. A female fluid connector portion according to claim 20 wherein the alignment guide includes at least one elongate recess for receiving an alignment prong of the male fluid connector portion.

22. A female fluid connector portion according to claim 20 wherein the alignment guide includes at least one visible marking.

23. A female fluid connector portion according to claim 20 comprising a cylindrical portion having a screw thread for engaging a complementary screw thread of the male fluid connector portion.

24. A female fluid connector portion according to claim 23 wherein the alignment guide includes at least one elongate recess for receiving an alignment prong of the associated male fluid connector portion, wherein a longitudinal axis of the at least one elongate recess is substantially parallel to a longitudinal axis of the cylindrical portion.

25. A female fluid connector portion according to claim 24 wherein, when the rotatable screw thread of the male fluid connector portion engages and is rotated relative to the screw thread portion of the female connector, hollow needles of the associated male connector portion are translated only in a direction that is substantially perpendicular to the plane of said septum seals.

26. A female fluid connector portion according to claim 20 comprising an outer casing having an annular end portion comprising a plurality of apertures through which the septum seal of each chamber can be accessed.

27. A female fluid connector portion according to claim 26 wherein the septum seal of each chamber is provided by a common annular, resilient, member retained against the inner surface of annular end portion.

28. A female fluid connector portion according to claim 20 wherein the septum seal of each chamber includes rubberised material.

29. A female fluid connector portion according to claim 20 wherein the septum seal is arranged to provide a fluidic seal that prevent egress of fluid through said septum seal when no needle is inserted therethrough.

30. A female fluid connector portion according to claim 20, wherein the female fluid connector portion is attached to a length of tubing having a plurality of lumens, each lumen being in fluid communication with one of said chambers.

31. A medical fluid connector for tubing having a plurality of lumens, the connector comprising:
   a male portion including a plurality of hollow needles, a distal end of each of the plurality of hollow needles including a sharp point, and
   a female portion including a plurality of septum seals through which said plurality of hollow needles can be passed and which prevents the egress of fluid when no needle is inserted therethrough, wherein the connector includes an alignment guide for uniquely aligning the hollow needles of the male portion with defined septum seals of the female fluid connector when the male fluid connector portion and the complementary female fluid connector portion are brought into engagement.

* * * * *